United States Patent [19]

Merrill, deceased et al.

[11] Plant 4,399

[45] Mar. 20, 1979

[54] PEACH TREE

[76] Inventors: Grant Merrill, deceased, late of Red Bluff, Calif.; by Lucille B. Merrill, executrix, 325 Breese Ave., Red Bluff, Calif. 96080

[21] Appl. No.: 890,577

[22] Filed: Mar. 20, 1978

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Roger B. Webster

[57] ABSTRACT

A peach tree which is of medium size and vigor, upright to spreading, vase formed, foliated with medium size, lanceolate leaves having a crenate to finely serrate margin, short petiole, and small, opposite, reniform glands, blooms with large, non-showy, rosy red flowers which are broad ovate to nearly round, and a regular and productive bearer of large to medium size, uniform, symmetrical, globose, mid-season, freestone fruit having yellow skin blushed with red, and yellow flesh, the surface of the pit cavity being a bright red.

1 Drawing Figure

BACKGROUND OF THE VARIETY

1. Field of the Invention

In an extensive plant breeding program, Grant Merrill originator and now deceased, originated a large number of new and distinct varieties of fruit trees, and which included the herein-claimed variety of peach tree. Such plant breeding program was undertaken in originator's experimental orchard located near Exeter, Tulare County, Calif.

2. Prior Varieties

Among the existent varieties of peach tree which were known to originator, particular reference is made to the Early O'Henry (U.S. Plant Pat. No. 3,583) and the July Lady (U.S. Plant Pat. No. 3,023).

ORIGIN OF THE VARIETY

The present variety of peach tree was originated, in the aforesaid experimental orchard, as a cross between the above-identified Early O'Henry and July Lady.

ASEXUAL REPRODUCTION OF THE VARIETY

When the seedling, of such cross, matured as a bearing tree, and it was determined to be of commercial value, the variety was asexually reproduced, on originator's behalf, by a commercial nursery, located at Madera, Madera County, Calif.; such reproduction having been accomplished by grafting on suitable rootstock. The asexual reproduction of the variety ran true, in all respects, to the original tree of the variety.

SUMMARY OF THE VARIETY

The herein-claimed new and distinct variety of peach tree is of medium size and vigor, upright to spreading, vase formed, foliated with medium size, lanceolate leaves having a crenate to finely serrate margin, short petiole, and small, opposite, reniform glands, blooms with large, non-showy, rosy red flowers which are broad ovate to nearly round, and a regular and productive bearer of large to medium size, uniform, symmetrical, globose, mid-season, freestone fruit having yellow skin blushed with red, and yellow flesh, the surface of the pit cavity being a bright red.

The herein-claimed variety of peach tree is further characterized in that its highly colored, firm fleshed, globose, freestone fruit is similar in shape to July Lady, but closely resembles Early O'Henry in skin and flesh color, and in firmness of the flesh; the harvest period, of the present variety, being between July Lady and Early O'Henry.

BRIEF DESCRIPTION OF THE DRAWING

The drawing is an illustration, by photographic reproduction in color, depicting fruit of the variety; certain of such fruit being shown whole, while others are cut into halves with the stone remaining in place in one of the related halves.

DESCRIPTION OF THE VARIETY

The botanical details of this new and distinct variety of peach tree—with color definitions (except those in common color terms) referenced to Maerz and Paul Dictionary of Color—are as follows:

Tree:
- *Size.*—Medium.
- *Vigor.*—Medium.
- *Growth.*—Upright to spreading.
- *Form.*—Vase-formed.
- *Hardiness.*—Hardy.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Grayish brown. Young branches — brownish green (15-L-6). Mature branches—bronze brown (16-C-9).
- *Lenticels.*—Number — Medium. Size — Medium.

Leaves:
- *Size.*—Medium. Average length — 18.25 cm. Average width — 3.75 cm.
- *Form.*—Lanceolate. Pointed.
- *Thickness.*—Thin.
- *Color.*—Top side — medium green (31-E-12). Under side — lighter green (21-I-8).
- *Texture.*—Smooth.
- *Margin.*—Crenate to finely serrate.
- *Petiole.*—Short — 1.1 to 1.4 cm. Thick to medium.

*Glands.*—Number — 2 to 4. Opposite. Small, relatively few, weak. Reniform. Position — apical on petiole.

*Stipules.*—Dehiscent.

Flower buds:

*Hardiness.*—Hardy.

*Size.*—Medium.

*Length.*—Medium.

*Form.*—Plump.

*Pubescence.*—Pubescent.

Flowers:

*Blooming period.*—Date of first bloom—Mar. 4, 1977. Date of full bloom —Mar. 11, 1977. Medium, as compared with other varieties.

*Size.*—Large. Average length — 15–16 mm. Average width — 13–15 mm.

*Form.*—Broad ovate to nearly round, with margins usually curled ventrally.

*Appearance.*—Non-showy.

*Color.*—Rosy red (1-F-3).

Fruit:

*Maturity when described.*—Hard — July 25, 1977.

*Date of first picking.*—July 20, 1977.

*Date of last picking.*—Aug. 2, 1977.

*Size.*—Uniform. Large to medium. Average diameter axially — 7.0 cm. Average transversely in suture plane — 7.4 cm.

*Form.*—Uniform. Symmetrical. Globose. One half usually very slightly larger than other half.

*Suture.*—Distinct. Shallow. Extends from base to beyond, but discontinuous at apex, with slight depression beyond pistil point.

*Ventral surface.*—Rounded slightly. Lipped throughout.

*Lips.*—Equal to unequal.

*Cavity.*—Flaring to abrupt. Elongated in suture plane, with suture showing on both sides usually. Depth — 1.2 to 1.7 cm. Breadth — 1.7 to 2.0 cm.

*Markings.*—None.

*Base.*—Broad-rounded to flat.

*Apex.*—Rounded to truncate.

*Pistil point.*—Apical. A very small, fleshy tip.

Skin:

*Thickness.*—Medium to thin.

*Texture.*—Medium.

*Tenacity.*—Tenacious to flesh.

*Tendency to crack.*—None.

*Down.*—Moderate. Short.

*Color.*—Ground color — Yellow (10-K-5) to (10-L-6). Blush — Orangy red (5-I-11) shading darker to Brickdust red (5-L-11).

Flesh:

*Color.*—Yellow (9-K-6). Surface of pit cavity — Bright red (6-L-6).

*Juice.*—Moderate.

*Texture.*—Firm. Fine. Meaty.

*Fibers.*—Fine. Tender.

*Ripens.*—Evenly.

*Flavor.*—Mild.

*Aroma.*—Distinct.

*Eating quality.*—Fair to good.

Stone:

*Type.*—Free. Parts from flesh smoothly.

*Size.*—Medium. Average length — 3.9 to 4.1 cm. Average breadth — 2.6 to 3.1 cm. Average thickness — 1.9 to 2.0 cm.

*Form.*—Oval.

*Base.*—Straight to slightly oblique ventrally.

*Hilum.*—Narrow. Oval.

*Apex.*—Acuminate.

*Sides.*—Unequal. Curved on right and left sides.

*Surface.*—Irregularly furrowed near base and ventral edge toward apex. Pitted toward base or from base to center.

*Ridges.*—Jagged.

*Pits.*—Circular to elongated.

*Ventral edge.*—Medium thickness. Without wing toward base.

*Dorsal edge.*—Narrow, with deep, narrow groove throughout.

*Color.*—Dark brown (8-A-12).

*Tendency to split.*—Slight.

Use: Market. Dessert.

Keeping quality: Good.

Resistance to insects and diseases: Good.

Shipping quality: Good.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, particularly characterized by its fruit being similar in shape to the July Lady, but having close resemblance in skin and flesh color, and in firmness of the flesh, to the Early O'-Henry; the harvest period of the present variety being between said July Lady and Early O'Henry.

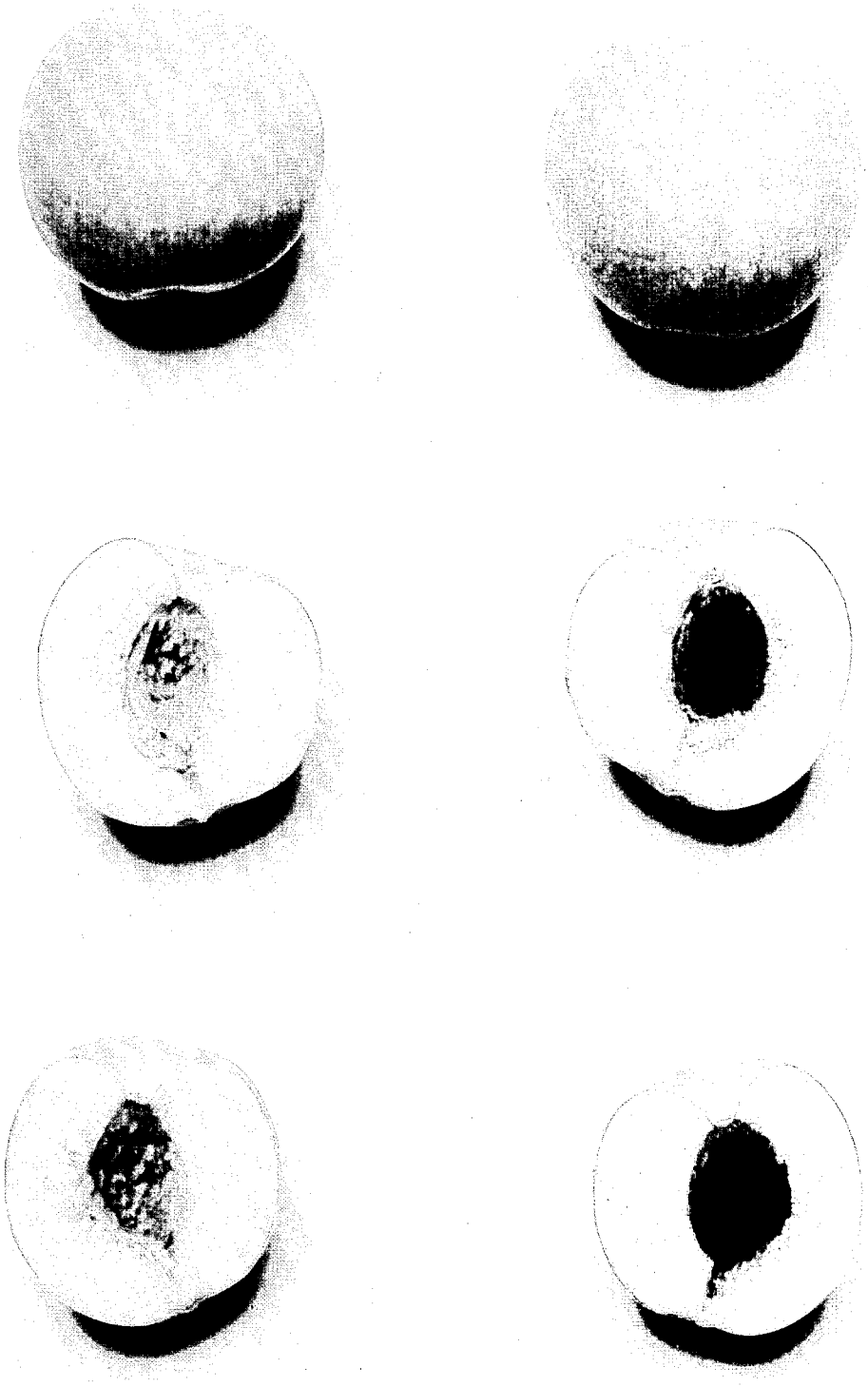

* * * * *